(12) United States Patent
Grosberg

(10) Patent No.: US 10,001,918 B2
(45) Date of Patent: Jun. 19, 2018

(54) METHOD AND SYSTEM FOR PROVIDING A SPECIALIZED COMPUTER INPUT DEVICE

(71) Applicant: Algotec Systems Ltd., Rochester, NY (US)

(72) Inventor: Ron Grosberg, Raanana (IL)

(73) Assignee: Algotec Systems Ltd., Ra'anana (IL)

(*) Notice: Subject to any disclaimer, the term of this patent is extended or adjusted under 35 U.S.C. 154(b) by 0 days. days.

(21) Appl. No.: 14/083,475

(22) Filed: Nov. 19, 2013

(65) Prior Publication Data

US 2014/0139465 A1 May 22, 2014

Related U.S. Application Data

(60) Provisional application No. 61/728,973, filed on Nov. 21, 2012.

(51) Int. Cl.
| | |
|---|---|
| G06F 3/041 | (2006.01) |
| G06F 3/0488 | (2013.01) |
| G06F 9/455 | (2018.01) |
| G06F 19/00 | (2018.01) |

(52) U.S. Cl.
CPC .......... G06F 3/04886 (2013.01); G06F 9/452 (2018.02); G06F 9/45512 (2013.01); G06F 19/321 (2013.01); G16H 40/63 (2018.01)

(58) Field of Classification Search
CPC .... G06F 3/04886; G06F 9/452; G06F 19/321; G06F 9/45512; G16H 40/63

USPC .......................................... 704/235; 345/173
See application file for complete search history.

(56) References Cited

U.S. PATENT DOCUMENTS

| | | | |
|---|---|---|---|
| 7,870,496 B1 * | 1/2011 | Sherwani | ...................... 715/761 |
| 8,271,908 B2 | 9/2012 | Li et al. | |
| 2007/0118400 A1 | 5/2007 | Morita et al. | |
| 2008/0183811 A1 | 7/2008 | Kotras et al. | |
| 2010/0033403 A1 | 2/2010 | Liao | |
| 2010/0070997 A1 * | 3/2010 | Friedman | .............. G06F 1/1626 |
| | | | 725/37 |
| 2011/0154228 A1 * | 6/2011 | Kinoshita | ...................... 715/763 |
| 2012/0046972 A1 * | 2/2012 | Tonti | .................... G06F 19/321 |
| | | | 705/3 |
| 2012/0185532 A1 | 7/2012 | Kristiansson et al. | |
| 2012/0297041 A1 * | 11/2012 | Momchilov | .......... G06F 9/4443 |
| | | | 709/223 |
| 2012/0324365 A1 * | 12/2012 | Momchilov | .............. G06F 3/14 |
| | | | 715/738 |
| 2013/0054240 A1 * | 2/2013 | Jang et al. | ..................... 704/235 |
| 2013/0127738 A1 * | 5/2013 | Miller | .................. G06F 3/0488 |
| | | | 345/173 |

OTHER PUBLICATIONS

European Search Report dated Jul. 17, 2014 for European Patent Application No. 13 020 129.6, 3 pages.

* cited by examiner

*Primary Examiner* — Jonathan Boyd

(57) ABSTRACT

A system and method for controlling a standalone computer through a separate touch screen input device.

28 Claims, 17 Drawing Sheets

METHOD AND SYSTEM FOR PROVIDING A SPECIALIZED COMPUTER INPUT DEVICE

CROSS REFERENCE TO RELATED APPLICATIONS

This application claims the benefit of U.S. Provisional application U.S. Ser. No. 61/728,973, provisionally filed on Nov. 21, 2012, entitled "METHOD AND SYSTEM FOR PROVIDING A SPECIALIZED COMPUTER INPUT DEVICE", in the name of Ron R. Grosberg, which is incorporated herein by reference in its entirety.

FIELD OF THE INVENTION

The present invention relates to a system and method for providing a specialized computer input device and particularly, but not exclusively, to the provision of such a device as a specialized medical keyboard.

BACKGROUND OF THE INVENTION

Computers were previously controlled only through keyboards, with the later addition of the computer "mouse" or pointing device. These input devices have the advantage of being operative with all computers but have the disadvantage of being difficult to fully customize, according to the needs of the user and/or of the software being operated by the computer.

With the advent of "smart" cellular telephones, also referred to as "smartphones", a new input device became popular, which is the touch sensitive screen, also referred to as a touch screen. For such devices, the display also doubles as an input device; the user touches various parts of the screen in order to cause the smartphone to perform various actions. Touch screens are also used for other types of portable computers, such as tablet computers.

Although touch screens provide a flexible GUI (graphical user interface) for user input, they are not a very useful input device on standalone computers, as the user has to reach out to interact with them. Furthermore, on standalone computers, the user needs to have the display screen clear to display data and information, such as images for example; displaying a set of icons and buttons for a user to access via a touch screen would interfere with this need.

It has been suggested that smartphones can be used to control other devices, such as televisions for example, acting as a "remote control"; the XBMC remote is an example of such a device. However, the capacity of such controls is very limited, as only a few control functions can be provided through the smartphone, and in any case, controlling a television does not require very many controls. Thus, there are currently no options for users of standalone computers, other than the standard keyboard and mouse, for controlling such computers through input devices.

SUMMARY OF THE INVENTION

The present invention, in at least some embodiments, provides a system and method for controlling a standalone computer through a separate touch screen input device, and in particular (in at least some embodiments) interfacing with a particular software program running on that computer such as a PACS (picture archiving and communication system) application. The software program is also described herein as an interactive software module. By "standalone computer" it is meant a computer which features a separate display screen and input device, such that the input device is separate from the display screen. For example and without limitation, the standalone computer, in the absence of the inventive separate touch screen input device, may optionally be controlled through a keyboard and/or through a mouse or other pointing device. Optionally, even when the inventive separate touch screen input device is present, the standalone computer may also optionally additionally be controlled through a keyboard and/or through a mouse or other pointing device.

The separate touch screen input device may optionally comprise any suitable device featuring a processor and a touch screen, including but not limited to a smartphone or a tablet.

The touch screen input device operates a virtualization program software module for providing a set of one or more simulated buttons, optionally in the form of keyboard keys; the virtualization program software module may also optionally provide a simulated track pad, track ball, mouse or other pointing device. Optionally, each one of the set of buttons, trackball, track pad, mouse or pointing device may be considered as an interaction element. Additionally, an interaction element can also be a gesture such as is common in touch screen based applications. These gestures include but are not limited to a long tap, double-tap, drag, flick, pinch and even shaking the device.

Optionally, the touch screen may also use a technology which creates physical buttons on its screen to enhance the user experience and provide a real key-press like feeling when using the program. A non-limiting example for such a technology is the one provided by Tactus Technologies® (http://tactustechnology.com).

The interaction elements may optionally be assembled to form a layout. The layout defines the location and type of various interaction elements to be displayed on the touch screen. Typical layouts contain a set of buttons which the user can press, possibly with a virtual mouse or trackpad or trackball or any combination of such elements. Additionally, the layout can contain a set of gestures that are enabled at various locations of the screen and with which the user can interact. The layout database optionally and preferably contains a collection of such predefined layouts.

The interaction elements in the layout may optionally have no specific connection to actual actions. They are optionally and preferably placeholders for operation assignments, which may optionally be more generally described as "functions" of the software which are performed according to user commands. In order to connect between the interaction elements and operation assignments that may be invoked by the user, preferably an operation assignment table is provided. The operation assignment table holds an association between an interaction element and the action that this interaction element performs. As such, a layout is a set of interaction elements numbered as e.g. Button#1, Button#2, etc . . . with Trackball#1 and so forth, and Mousepad#1 and so forth, while the operation assignment table preferably comprises entries that assign e.g. operation#j to Button#i. The set of operations can be standard operations such as mouse move, double click, a certain keyboard key or keyboard key combination such as Alt-J (also known as keyboard "shortcuts), or windows (GUI—graphical user interface) based commands such as minimizing or dragging a window. In addition, they may also comprise logical operations relevant to the specific software program that is being controlled through the touch screen device, such as zoom or pan in image processing or manipulation programs.

As described herein, the combination of layout and operation assignments for the interaction elements is referred to as a desktop. The virtualization program allows the user to switch between various desktops, or alternatively to create a new desktop according to the wishes of the user. Creating a desktop involves determining a layout, for example optionally by choosing a layout from a set of predefined layouts and assigning operation assignments from the operations database to that layout. Virtualization program also allows the user to design or enter a specialized layout, for example optionally from an external source, or alternatively by providing a "canvas" or interaction platform through which the user can draw interaction elements on a user interface which the virtualization program knows how to interpret.

The virtualization program allows the user to choose a desktop to work with. Alternatively, the desktop can be chosen according to one or more external parameters, for example related to the operations of software on the standalone computer.

According to at least some embodiments, the present invention provides a system and method for a user to interact with image processing software on a standalone computer, for example for medical image processing software. Such software allows skilled medical personnel, such as doctors, to view, manipulate and interact with medical images such as CT (computerized tomography) scans, MRI (magnetic resonance imaging) scans, PET (positron emission tomography) scans, mammography scans and the like. For the field of medical image processing, it is important to be able to accurately, rapidly and reliably perform various processes such as segmentation, as medical diagnoses increasingly rely upon such information. Therefore, doctors need to be able to accurately and rapidly interact with medical image processing software.

Currently, doctors need to page through various menus through a GUI, remember various keyboard key combinations for "shortcuts" or purchase a specialized keyboard; the last option does provide additional keyboard-based interactive options but may not be suitable for the doctor's needs and in any case cannot be customized. Additionally, medical image reading is often done in low lighting conditions in order to better view the images. In such circumstances, the backlit nature of handheld devices such as tablets provides a much clearer interaction with virtual keyboard.

U.S. Pat. No. 7,870,496 to Sherwani describes a system using touchscreen user interface of a mobile device to remotely control a host computer. The present invention, in various embodiments, may be distinguished over this reference in a number of different ways. Without wishing to be limited by a closed list, among the various differences between the present invention, in various embodiments, and this reference includes the lack of any support or description for user defined interaction elements and desktops related to a specific interactive software in the reference. Furthermore, again without wishing to be limited by a closed list, the reference fails to disclose any of the following features: verbal dictation converted to text; transfer of data, such as patient data, between the host computer and the touchscreen device, and use with medical imaging software.

US2012/0297041 to Momchilov describes a system using touchscreen user interface of a mobile device to remotely control a host computer. The present invention, in various embodiments, may be distinguished over this reference in a number of different ways. Without wishing to be limited by a closed list, among the various differences between the present invention, in various embodiments, and this reference includes the lack of any support or description for user defined interaction elements and desktops related to a specific interactive software in the reference. Furthermore, again without wishing to be limited by a closed list, the reference fails to disclose any of the following features: verbal dictation converted to text; transfer of data, such as patient data, between the host computer and the touchscreen device, and use with medical imaging software.

Although the present description centers around interactions with medical image data, it is understood that the present invention may optionally be applied to any suitable three dimensional image data, including but not limited to computer games, graphics, artificial vision, computer animation, biological modeling (including without limitation tumor modeling), graphical design programs, CAD/CAM software, and the like; the present invention may also optionally be applied to any software program that is not image based or image analysis based including but not limited to word processing programs and other office programs, and so forth.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIG. 9A shows the partially populated layout with a trackball; FIG. 9B shows the completely populated layout as a desktop with a trackpad; and FIG. 9C shows the completely populated layout as a desktop with buttons only;

DESCRIPTION OF EMBODIMENT OF THE INVENTION

Unless otherwise defined, all technical and scientific terms used herein have the same meaning as commonly understood by one of ordinary skill in the art to which this invention belongs. The materials, methods, and examples provided herein are illustrative only and not intended to be limiting.

This application claims the benefit of U.S. Provisional application U.S. Ser. No. 61/61/728,973, provisionally filed on Nov. 21, 2012, entitled "METHOD AND SYSTEM FOR PROVIDING A SPECIALIZED COMPUTER INPUT DEVICE", in the name of Ron R. Grosberg, which is incorporated herein by reference in its entirety.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Although the present invention is described with regard to a "computer" on a "computer network", it should be noted that optionally any device featuring a data processor and the ability to execute one or more instructions may be described as a computer, including but not limited to any type of personal computer (PC), a server, a cellular telephone, an IP telephone, a smart phone, a PDA (personal digital assistant), or a pager. Any two or more of such devices in communication with each other may optionally comprise a "computer network".

Although the present description centers around medical image data, it is understood that the present invention may optionally be applied to any suitable three dimensional image data, including but not limited to computer games, graphics, artificial vision, computer animation, biological modeling (including without limitation tumor modeling) and the like.

At least some embodiments of the present invention are now described with regard to the following illustrations and accompanying description, which are not intended to be limiting in any way.

Figure 1:
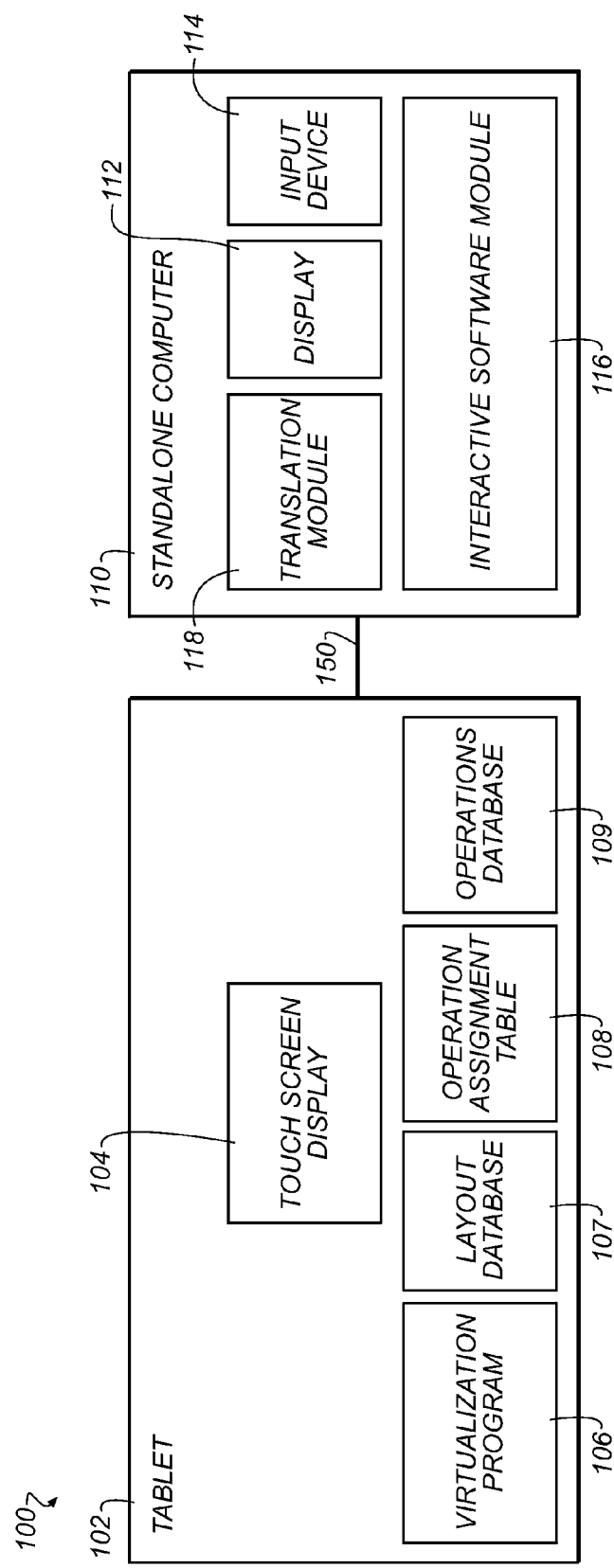
FIG. 1 shows an exemplary, illustrative system according to at least some embodiments of the present invention for providing a touch screen input device to a standalone computer.

Referring now to the drawings, FIG. 1 shows an exemplary, illustrative system according to at least some embodiments of the present invention for providing a touch screen input device to a standalone computer. As shown, a system 100 features a tablet 102, having a touch screen 104 and operating a virtualization program 106, a layout database (107), an operations database (109) and an operation assignment table (108).

Tablet 102 may optionally be any type of input device having a processor and touch screen 104, such as a tablet computer, a smartphone and so forth. Tablet 102 operates virtualization program 106, which is a software module for providing a flexible keyboard containing interaction elements for display to, and interaction with, the user. Virtualization program 106 causes the keyboard to be displayed to the user through touch screen 104; as the user manipulates different parts of touch screen 104, virtualization program 106 is able to interpret these manipulations as though the user were manipulating the interaction elements. Preferably, the display shown to the user through touch screen 104 is of a set of virtual buttons, optionally along with one or more additional interaction elements such as discussed above. These virtual buttons may include keys as in a normal keyboard, but also custom buttons containing custom operations.

Tablet 102 is in communication with a standalone computer 110 through a connection 150; connection 150 may optionally be wired or wireless, for example including but not limited to WiFi, Bluetooth, InfraRed or any other type of wireless communication. As virtualization program 106 interprets the interactions of the user with touch screen 104 as manipulating the interactions elements, these interaction elements are translated via the operation assignment table 108 into the operations matching the interaction elements. These operations are sent to standalone computer 110 through connection 150.

As shown, standalone computer 110 features a display 112, an input device 114 and an interactive software module 116. Standalone computer 110 operates interactive software module 116 to perform some actions desired by the user, such as for example and without limitation, image processing software to display, review and interact with images. The present invention encompasses any suitable interactive software within the boundaries of interactive software module 116; word processing programs and other office programs, graphical design programs, CAD/CAM software and so forth, are all encompassed as non-limiting examples thereof.

Display 112 is optionally any suitable type of computer display; it may optionally be integrated with, or separate from, the other components of standalone computer 110 (for example and without limitation, in a desktop computer as opposed to a laptop or portable computer). Input device 114 may optionally comprise a keyboard or mouse or other pointing device, or a combination of such devices, such as for example a keyboard and a mouse.

In the absence of tablet 102, the user would interact with standalone computer 110 through input device 114 alone (which as noted above may optionally comprise a plurality of such devices) to interact with and control interactive software module 116. However, system 100 enables the user to interact with standalone computer 110 through tablet 102, in addition to, or in place of, input device 114. The user is able to interact with and control interactive software module 116 through tablet 102.

As previously described, layout database 107 comprises a plurality of layouts (also discussed in greater detail with regard to FIGS. 3 and 4 below); operations database 109 comprises a plurality of identified operation functions for performing one or more interactions with interactive software module 116, while operation assignment table 108 relates to the specific operation functions assigned to each interaction element of each layout. The interaction of these various components is also described in greater detail with regard to FIGS. 3 and 4 below.

In operation, the user interacts with the set of interaction elements provided by tablet 102 through touch screen 104. As noted previously, virtualization program 106 converts the interaction elements into operations. Such operations are sent to standalone computer 110 through connection 150 and are received by a translation module 118, which is operated by standalone computer 110. Translation module 118 translates the operations into commands for interactive software module 116, which then performs the user requested action(s).

Optionally, interactive software module 116 incorporates part or all of the functionality of translation module 118. Alternatively, interactive software module 116 is adjusted in one or more functions so that the operations received by translation module 118 are translated directly into commands for interactive software module 116. If interactive software module 116 is not adjusted in any way, then translation module 118 may need to translate the operations it receives into commands that rely upon a traditional GUI layout for interactive software module 116. For example and without limitation, a command that would normally require a mouse click on a specific button or menu of interactive software module 116, would be activated by translation module 118 moving the mouse cursor to the coordinates on the screen where the button or menu is located and then simulating a mouse click so that the button or menu would be activated. Various combinations of these scenarios are also possible as described further below with reference to FIG. 5.

The user is preferably able to change the layout displayed by tablet 102 for customization. As described in greater detail below with reference to FIGS. 3 and 4 and with reference to the screenshots of FIGS. 8-10, virtualization program 106 is optionally in communication with a database (not shown), preferably located at tablet 102, which contains a plurality of interaction elements. The user is presented with a list of choices for selecting such interaction elements; virtualization program 106 may also optionally be able to present one or more predetermined layouts, with or without one or more preselected interaction elements, also as described in greater detail below with reference to FIG. 3 and with reference to the screenshot of FIG. 8. Once the user has selected or created a layout of interaction elements and assigned one or more operations to these interaction elements, then the user determined desktop (the combination of layout, interaction elements and operations) is displayed by tablet 102.

As a non-limiting example, if interactive software module 116 comprises medical imaging software, for viewing medical images, then virtualization program 106 may optionally feature one or more predetermined desktops. The user may optionally select from such desktops or create a new one. The desktops may for example optionally be designed to be most suitable for reading and interpreting certain types of medical images, such as mammography (as in FIG. 9B), ultrasound and so forth. The desktops may also optionally be further specialized, so as to be specialized for ultrasound for a particular body part or area for example. Thus, virtualization program 106 may optionally be adapted for particular types of software or software functions.

Optionally, as described in greater detail below with reference to FIG. 12, a user may share a particular layout or desktop for a particular type of software or software function with members of a community, which share such layouts or desktops through the Internet for example.

Translation module 118 may also optionally cause user interactions with the desktop on tablet 102 to be translated to direct commands to interactive software module 116. In order to accomplish this, interactive software module (116) needs to be modified so that it can interpret such commands. For example, suppose that interactive software module 116 comprises a PACS application such as a PACS viewer. One common operation for such applications is a panning operation for an image, which in this case would be a medical image. In order to support the panning operation through the tablet, touch screen display 104 would preferably display a virtual button or other interaction element on the desktop that embodies a panning operation for a medical image. The PACS viewer application (interactive software module 116) could optionally be modified to accept instructions from an external interactive device such that when the virtual panning button is pressed, the virtualization program 106 translates this into a pan operation command that is sent to translation module 118. The translation module 118 sends a pan operation to the PACS viewer application. Since the PACS viewer application was modified to accept commands from external applications, the PACS viewer application interprets the operation as a command to switch to pan mode. Once switching to pan mode future mouse movements on standalone computer or interaction with the assigned panning element on tablet 102 will cause a panning operation for the images being displayed through display 112.

Optionally, tablet 102 may also optionally feature reporting or reporting support functions, such as a microphone (not shown) and the ability to receive dictation from the doctor or other user. In this embodiment, tablet 102 would receive dictation from the user and would either perform speech-to-text conversion or alternatively would send the voice data to a remote location for such conversion, including but not limited to standalone computer 110 or a remote server, such as remote server 224 of FIG. 2. Optionally, tablet 102 would only act to receive the voice data and would send such data to standalone computer 110; optionally and preferably translation module 118 receives such data, along with a command indicating that it is voice data, and then forwards the data to the appropriate application (whether as a voice command that needs to be translated into an action or for voice to text conversion).

Figure 2A:
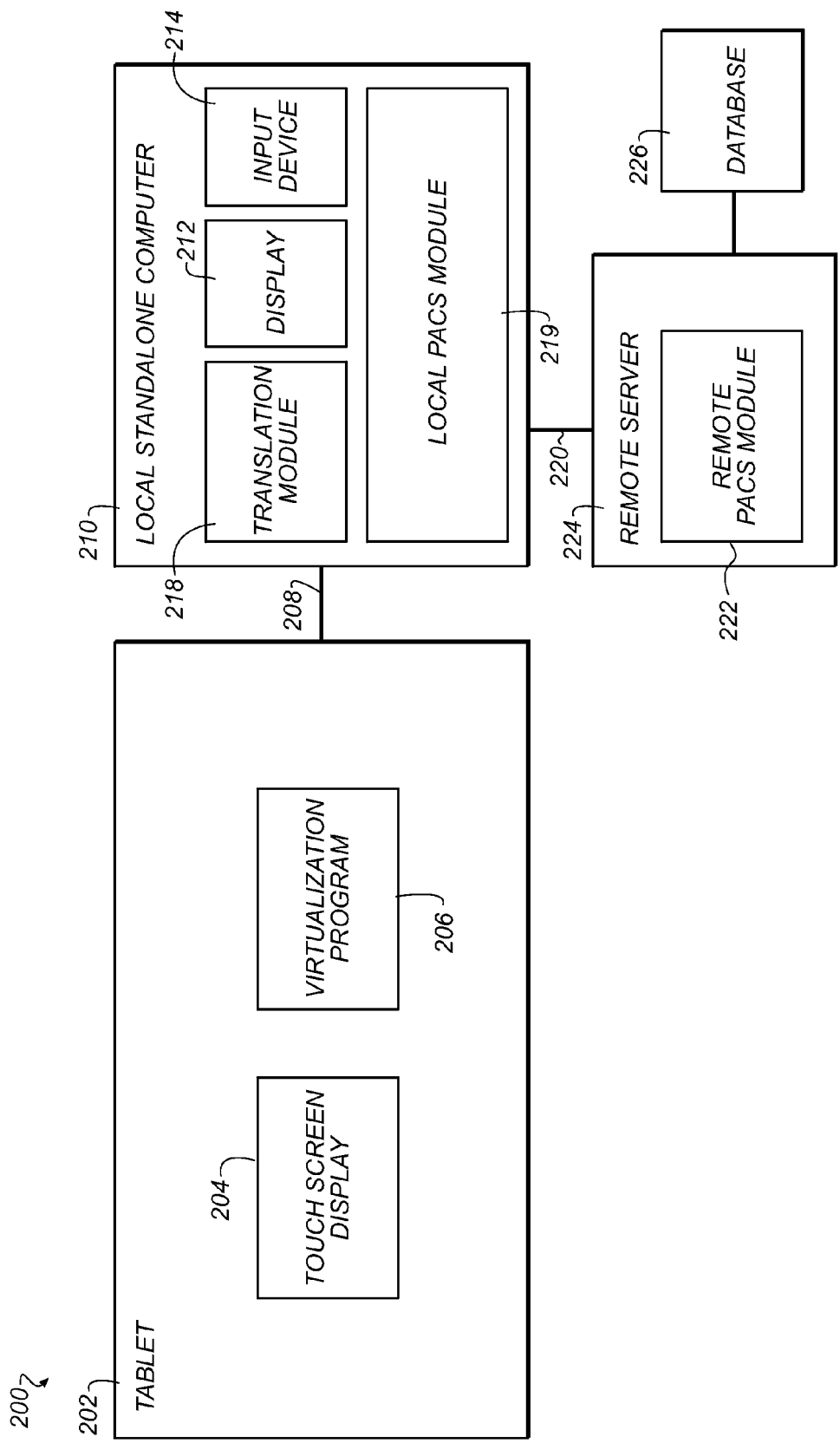
FIG. 2A shows an illustrative embodiment of an exemplary, illustrative system for providing a touch screen input device to a standalone computer for supporting user interactions with medical imaging software.

FIG. 2A shows a specific illustrative embodiment of an exemplary, illustrative system for providing a touch screen input device to a standalone computer for supporting user interactions with medical imaging software. Items with the same reference end number as components in FIG. 1 have at least a similar or related function, for example touch screen display (104) of FIG. 1 has the same functionality as touch screen display (204) of FIG. 2.

As shown in FIG. 2A, in a system 200, tablet 202, touch screen display 204 and virtualization program 206 are present as for system 100, with similar functions. For the sake of clarity only and without any intention of being limiting in any way, layout database (107), operations database (109) and operation assignment table (108) are not shown.

Virtualization program 206 is specifically adapted for use with medical imaging software, which in this non-limiting example is shown as a PACS module, whether as a local PACS module 219, a remote PACS module 222 or a combination thereof.

Local PACS module 219 is optionally located at a local standalone computer 210, while remote PACS module 222 is optionally instead operated by a remote server 224, all of which preferably communicate through a computer network 220. Computer network 220 may optionally be any type of computer network, such as the Internet for example. Further instances of local standalone computers running local PACS modules (not shown) may also access remote PACS module 222 on remote server 224.

In this example, translation module 218 sends translated commands received from virtualization program (206) to local PACS module 219, which then performs one or more functions according to the translated commands. Optionally translation module 218 may send one or more commands received from virtualization program (206) directly to display 212, for example to alter a GUI display being displayed through display 212; local PACS module 219 is then preferably updated with regard to the command being transmitted.

Optionally, if medical images are not stored locally to local standalone computer 210, then even if local standalone computer 210 operates local PACS module 219, commands to retrieve images may optionally be sent to remote server 224. It should be noted that remote server 224 may optionally comprise a plurality of processors and/or a plurality of computers and/or a plurality of virtual machines, as is known in the art.

Interaction between virtualization program (206) and PACS module (219) may also be bi-directional so that the touch screen display shows information or performs tasks according to the current state of the PACS module (219). For example, the PACS viewer can send the details of the patient of which images are currently showing so that the touch screen will show them clearly for the doctor to see. It can also send a link of these images upon user request so that the user may see these images in a web-viewer connected to the same PACS archive (such as remote PACS module 222), or hold the details of the currently displayed scan to be able to open it from a different standalone computer, e.g. when the doctor wants to continue working from home on the same case he was working on in the hospital, as described in greater detail below with reference to FIG. 2B.

The bi-directional nature of the virtualization program (206) enhances its role as providing the user with a single user experience across different systems (e.g. between his/her computer at home and at the office), and provides a method to "communicate" between systems. For example, if the user is a doctor, then the doctor may be working at a clinic on a case and decides to continue the work at home. The PACS module has the capability to save the current work-view of a study so that when the study is reloaded the same view is presented to the doctor. This "save current view" command is accessible from the PACS module which is also controlled from the virtualization program 206 on the tablet. Therefore, a virtual key can be set up on the tablet which activates the "save current view" command on the standalone computer.

Figure 2B:
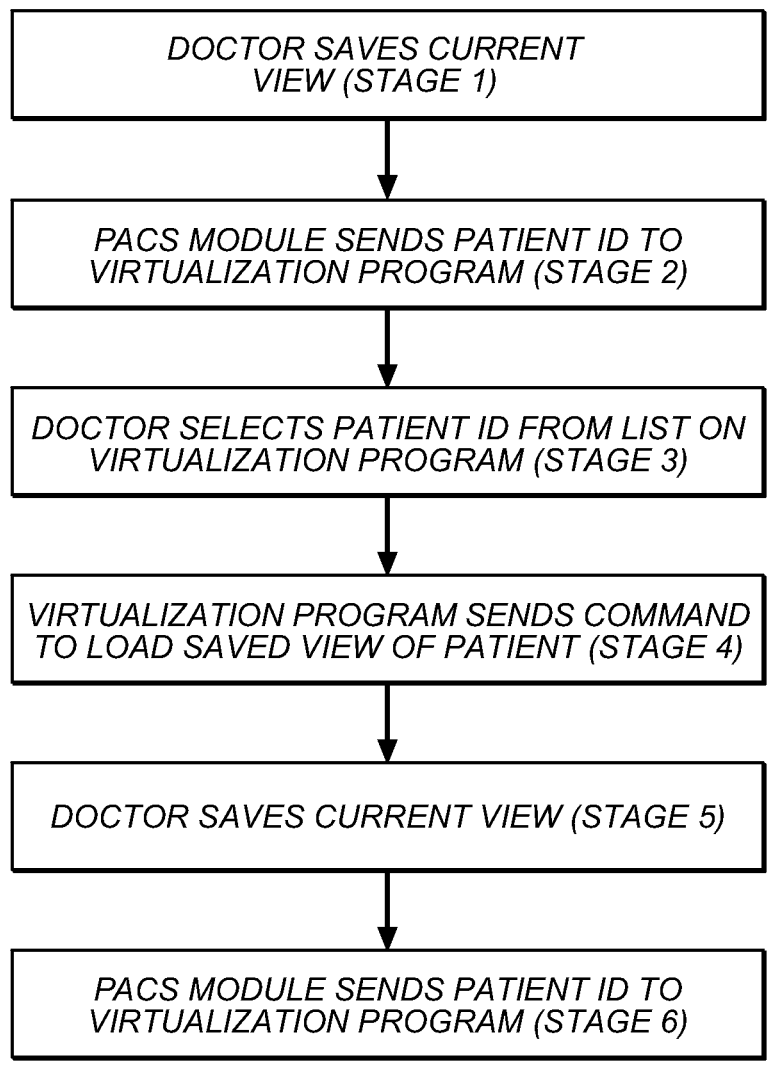
FIG. 2B shows an exemplary, illustrative method according to at least some embodiments of the present invention for transferring information between medical imaging software and a touch screen input device.
Figure 11:
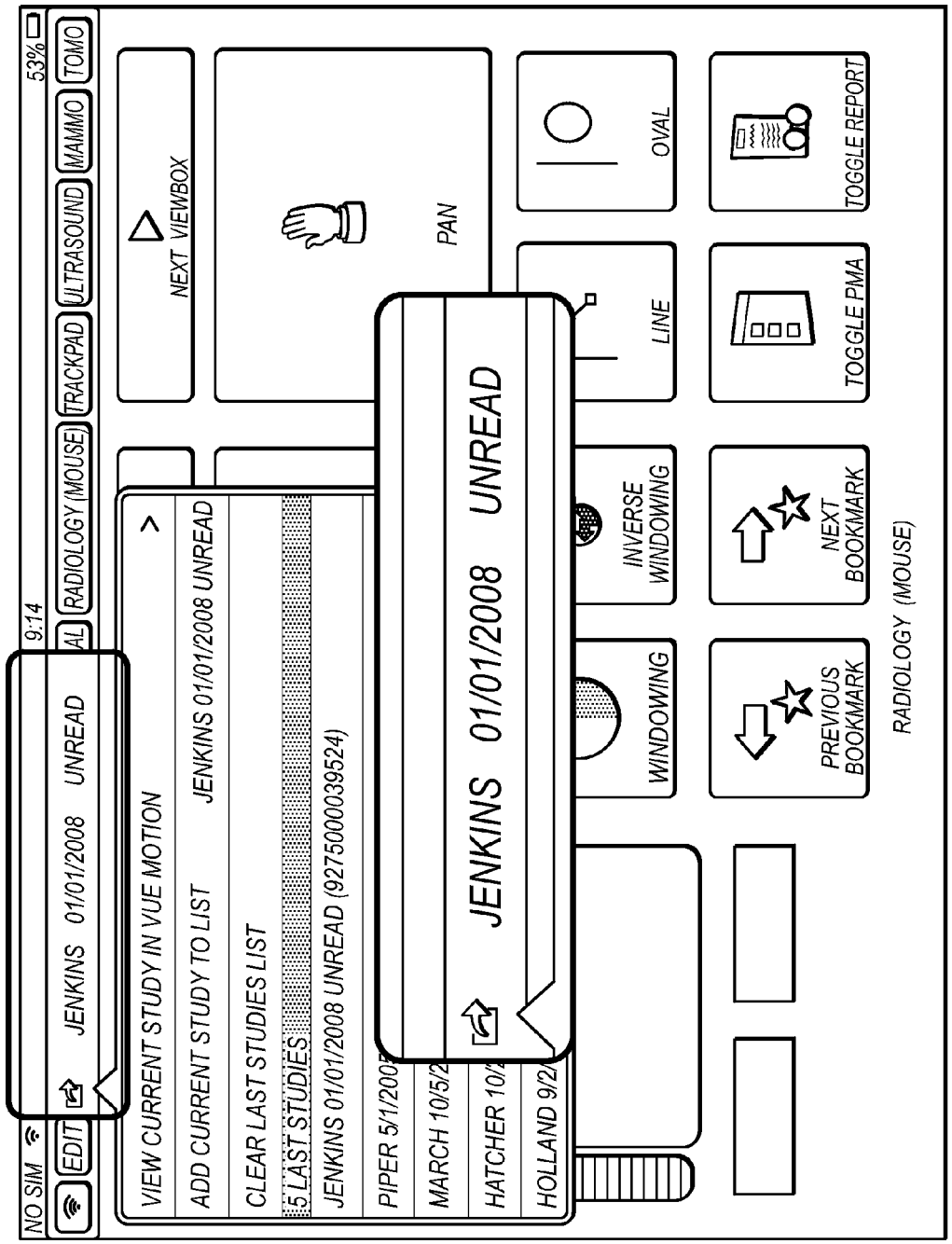
FIG. 11 shows the ability to obtain further information from the PACS software, shown in an optional thin client configuration.

Referring now to FIG. 2B, in Stage 1, the doctor chooses the "save current view" command—either directly via the input device on standalone computer 210 or via virtualization program 206. In Stage 2 the PACS module sends a patient ID, representing the patient whose images were being viewed, to the virtualization program 206 where it is stored in a list along with other patients. Such a list is shown in the screenshot of FIG. 11. The doctor takes the tablet, which may be his own or the clinic's, home with him.

The doctor begins work at home optionally using a PACS module on a local computer accessing remote server 222 where the images are stored. In Stage 3 the doctor selects the patient ID from the list on the virtualization program of the tablet. In Stage 4 the virtualization program sends a command to the local PACS module to load the images of the patient in the specific view that existed when the "save current view" command was activated. When the doctor stops working at home the process can be repeated as at Stage 5 where the doctor once again activates the "save current view" command. In Stage 6 the ID of the viewed patient is again added to the list of virtualization program 206 so that it may be retrieved the next day when the doctor wishes to access the same patient and view.

The bi-directional communication between virtualization program 206 and PACS module 219 thus enables an enhanced workflow for users.

Figure 3:
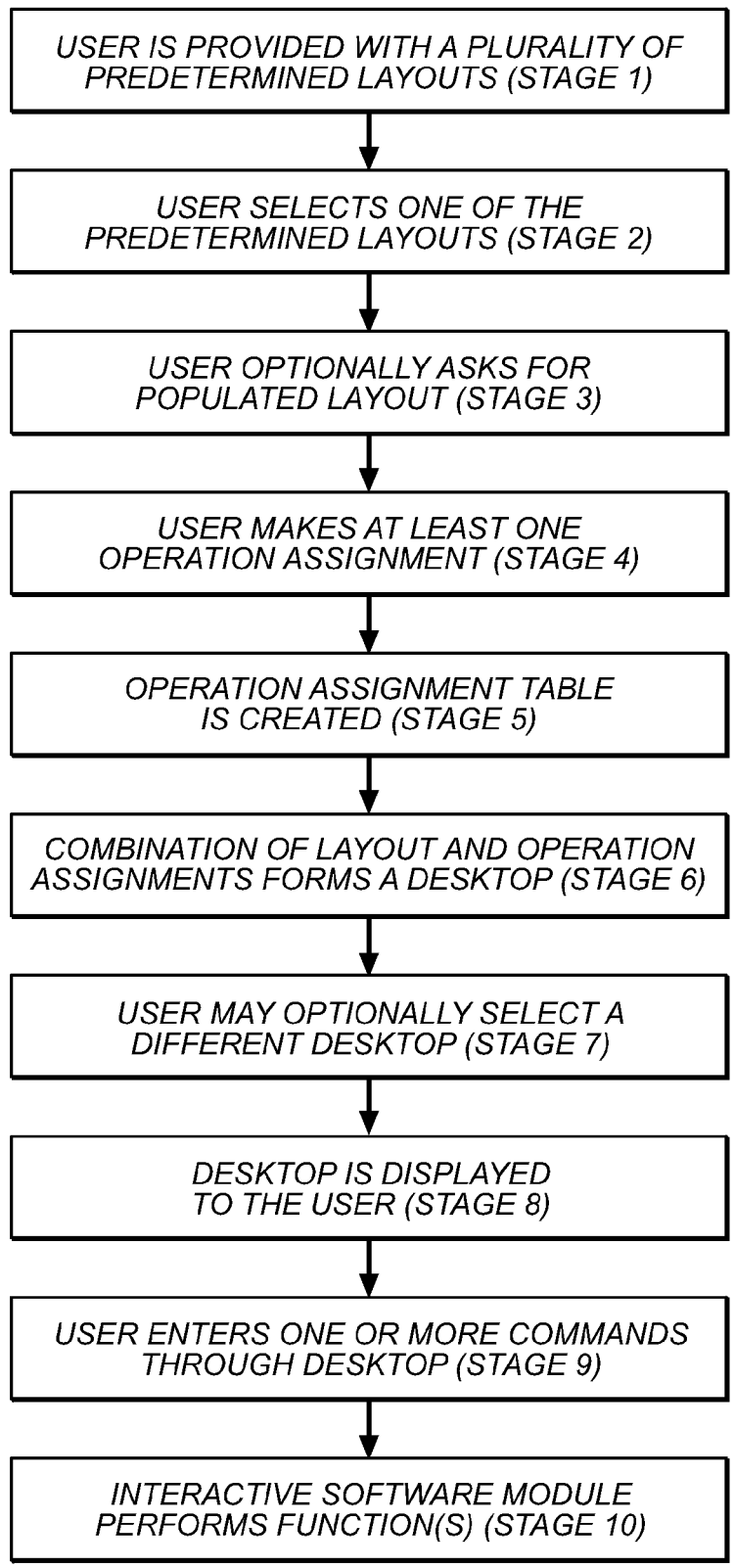
FIG. 3 shows an exemplary, illustrative method according to at least some embodiments of the present invention for determining a virtual keyboard by a user and for operating an interactive software module through the virtual keyboard.

FIG. 3 shows an exemplary, illustrative method according to at least some embodiments of the present invention for selecting a desktop by a user and for operating an interactive software module through the desktop. As described above, a desktop comprises a layout combined with operations assigned to interaction elements.

In Stage 1, the user is provided with a plurality of predetermined layouts, comprising a plurality of interaction elements; as previously described, each one of buttons, trackball, track pad, mouse or pointing device may be considered as an interaction element. Additionally, an interaction element can also be a gesture such as is common in touch screen based applications. These gestures include but are not limited to a long tap, double-tap, drag, flick, pinch and even shaking the device. However, in this Stage, the user is preferably provided with a plurality of such layouts in which functions have not been assigned to the interaction elements.

Preferably these predetermined layouts are provided through the previously described virtualization program and are stored in the previously described layout database.

Optionally the layouts are connected to a particular interactive software module and/or to a particular type of data being analyzed or manipulated by the software module. One example of the former would be providing a plurality of layouts that are suitable for a CAD-CAM program or for an image processing program; presumably the suitable layouts would be different for each type of software program.

Furthermore, even within a category or type of software program, different layouts may optionally be offered as suitable according to the type of data being analyzed. For example, CAD-CAM programs for design machine parts would presumably have different needs and uses than other types of CAD-CAM programs. In terms of image analysis, medical image analysis software has different requirements as compared to other types of image analysis software; furthermore, even when analyzing medical image data, different types of medical image data also have different functions and requirements for the interactive software module, as for example when analyzing mammography data as opposed to ultrasound data, for example.

The provided predefined layout examples optionally and preferably define the location and type of various interaction elements to be displayed on the touch screen. Typical layouts contain a set of buttons which the user can press, possibly with a virtual mouse or trackpad, or alternatively or additionally through direct touch, and gestures that are enabled at various locations of the screen. The layout database optionally and preferably contains a collection of such predefined layouts.

At this stage, the interaction elements in the layout may optionally have no specific connection to actual actions. They are optionally and preferably placeholders for operation assignments, which are assignments that connect the interaction elements to specific functions of the interactive software module.

In Stage 2, the user selects one of the provided predetermined layouts (a non-limiting example of a method to create such a layout is described with reference to FIG. 4 in more detail).

In Stage 3, the user may optionally ask the virtualization program to have the layout prepopulated with operation assignments of the interaction elements, for example optionally according to one or more stored completed layouts with such assignments already made.

Alternatively or additionally in Stage 4, the user may optionally choose to make at least one operation assignment of an interaction element, whether starting from the prepopulated layout and making one or more changes, or alternatively by having the user start from "scratch" without any such pre-assignments. The operations that can be assigned are selected from a defined list based on the capabilities of the particular interactive software module and/or to a particular type of data being analyzed or manipulated by the software. The operation database containing the defined list is preferably provided along with the virtualization program.

In Stage 5, once the operation assignments of the interaction elements have been made, then an operation assignment table (108 of FIG. 1) is created. As previously described, the tablet or other handheld touchscreen device preferably operates the operations database (109), which includes all of the different functionalities of the interactive software for which an operation may be assigned, optionally apart from the operation assignment table itself. Optionally, the table may be created and populated as part of Stage 4.

The operation assignment table holds an association between an interaction element and the action that this interaction element performs. As such, a layout is a set of interaction elements numbered as e.g. Button#1, Button#2, etc . . . with Trackball#1 and so forth, and Mousepad#1 and so forth, while the operation assignment table preferably comprises entries that assign e.g. operation#j to Button#i. The set of operations can be standard operations such as mouse move, double click, a certain keyboard key or keyboard key combination such as Alt-J (also known as keyboard "shortcuts"), or windows (GUI—graphical user interface) based commands such as minimizing or dragging a window. In addition, they may also comprise logical operations relevant to the specific software program that is being controlled through the touch screen device, such as zoom or pan in image processing or manipulation programs.

In Stage 6, the combination of the layout and the operation assignments forms a desktop, which may optionally be saved by the user for later use, for example optionally according to the combination of the selected layout and the operation assignment table.

In Stage 7, the user may optionally select a different desktop, as the previously determined desktop may optionally not be suitable for a particular software or data analysis. Virtualization program 106 allows the user to switch between various desktops.

In Stage 8, regardless of whether the same or a different desktop has been selected, the desktop is displayed to the user through the touch screen display, ready for accepting one or more user commands for interacting with the interactive software module 116. Optionally, the process may start from this stage such that previous stages are not performed.

In Stage 9, the user enters one or more commands through the desktop by interacting with one or more interaction elements, for example by pressing one or more virtual buttons. In Stage 10, the entering of such commands causes the interactive software module on the standalone computer to perform one or more functions; typically but not necessarily, such functions lead to one or more changes to the information, image or data being displayed on the display of standalone computer.

As a non-limiting example, if the interactive software module comprises a PACS application such as a PACS viewer, then the one or more commands entered by the user could optionally cause a change in the displayed image, which in this case would be a medical image. One common operation for such applications is a panning operation for the medical image. In order to support the panning operation through the virtual desktop, the touch screen display would preferably display a virtual button or other interaction element on displayed virtual desktop that embodies a panning operation for a medical image, which the user would then depress or otherwise interact with in Stage 9. The PACS viewer application could optionally be modified to accept instructions from the translation module, as previously described, such that when the virtual panning button is pressed, the PACS viewer would switch to pan mode (that is to "pan" along the image or images) whereupon movements of the mouse or alternatively the virtual mousepad on the tablet will perform "panning" functions which cause a difference in the image or images being displayed in Stage 10.

Figure 4:
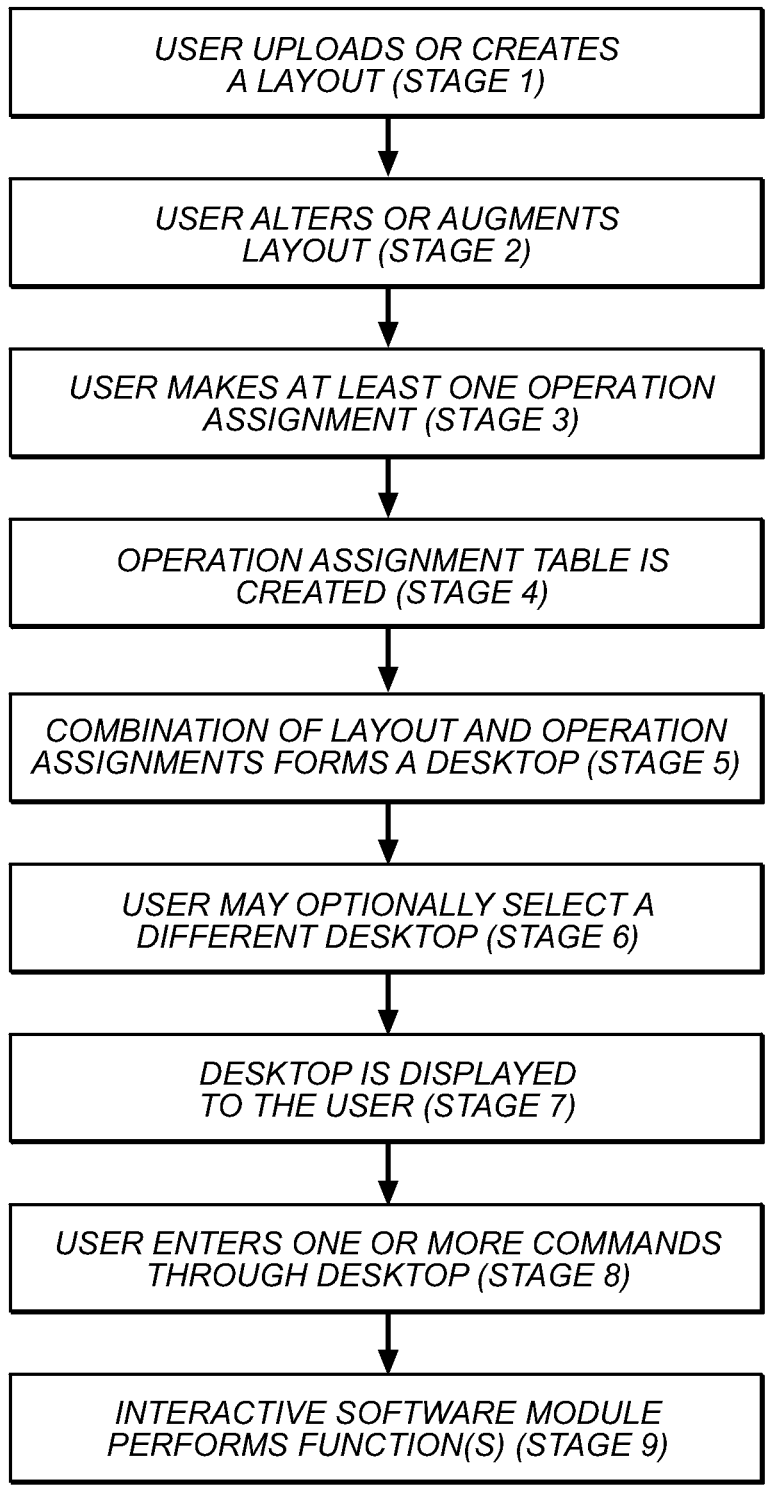
FIG. 4 shows an exemplary, illustrative method according to at least some embodiments of the present invention for creating a virtual keyboard by a user and for operating an interactive software module through the virtual keyboard.

FIG. 4 shows an exemplary, illustrative method according to at least some embodiments of the present invention for creating a virtual keyboard by a user and for operating an interactive software module through the virtual keyboard. In FIG. 3, the user was presented with various predetermined layout choices and selected from those choices, optionally with alterations. However, this method relates to a process in which the user creates the layout and from that layout, the virtual keyboard.

In Stage 1, the user either uploads a previously created layout design or uses an interactive tool to create a layout design. For example and without limitation, the software may optionally provide a "canvas" or interaction platform through which the user can draw interaction elements on a user interface which the virtualization program knows how to interpret, on which the user can create the layout, optionally from various predetermined components.

In Stage 2, the user is optionally provided with various choices to augment or alter the layout, for example according to the type of interactive software program with which the user wishes to use the virtual keyboard. Also in this stage, the user needs to complete any interaction element assignments to the layout, if these assignments were not made in Stage 1.

Stages 3-9 of FIG. 4 correspond to Stages 4-10 of FIG. 3 and are performed in a similar or identical manner.

Figure 5:
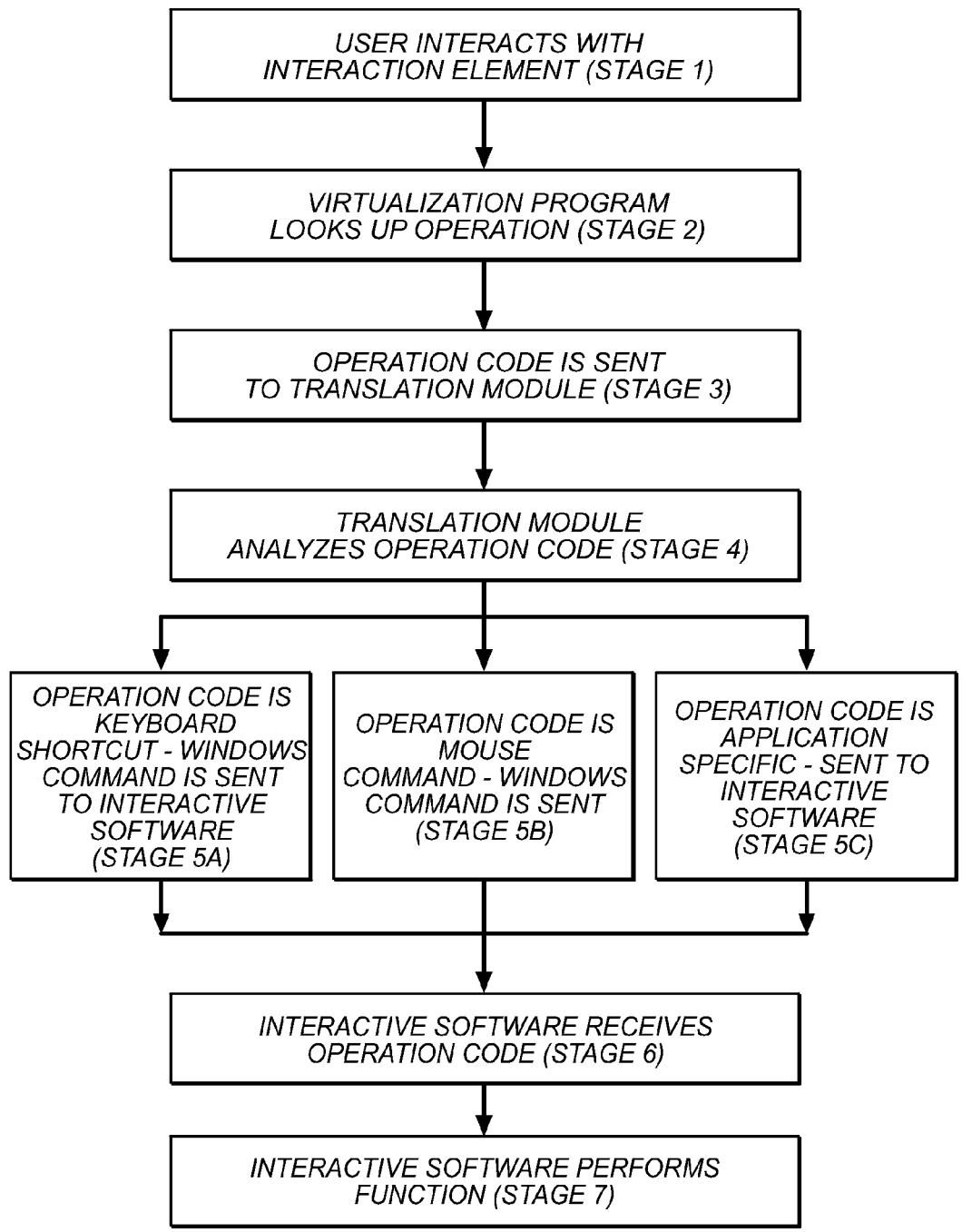
FIG. 5 relates to a method for operating the virtual keyboard by the user, in terms of the "back office" actions performed by the virtualization program and the interactive software.

FIG. 5 relates to a method for operating the virtual keyboard by the user, in terms of the "back office" actions performed by the virtualization program and the interactive software. In Stage 1, as previously described, the user interacts with an interaction element, for example by pressing a virtual button on the virtual keyboard. In Stage 2, the virtualization program looks up the operation identified according to that interaction element, for example by determining the operation code. In Stage 3, the operation code is sent to the translation module, from the tablet or other touch screen display device to the standalone computer. In Stage 4, the translation module receives the operation code and analyzes it. The method then splits according to the analysis of the operation code.

In Stage 5A, if the operation code is a keyboard shortcut (that is, representing a combination of keys on the keyboard), then the translation module sends the key combination to the interactive software module via the operating system simulating the pressing of the keys required. If the operation code is for an operation for a mouse or other pointing device, then the translation module sends the operation as a command to windows (i.e.—to the operating system) in Stage 5B i.e.: the mouse cursor is moved on screen and "clicks" as if it had been controlled by the mouse connected to standalone computer. If the operation code is an application specific operation for the interactive software module, then in Stage 5C the translation module sends an appropriate command to the interactive software module using the specific protocol that is accepted by or incorporated into the interactive software module.

In Stage 6, the interactive software module receives the operation code, optionally only if Stage 5C is performed as described above, but alternatively for any of the above stages of Stage 5. If the latter, then if the operation code relates to an operating system (windows) message or keyboard message, then these operations are handled as they are normally handled. If an operation code for the interactive software module, then in Stage 7 this module issues an operation command according to code (in other words, the module performs the necessary function according to the code).

Figure 6A:
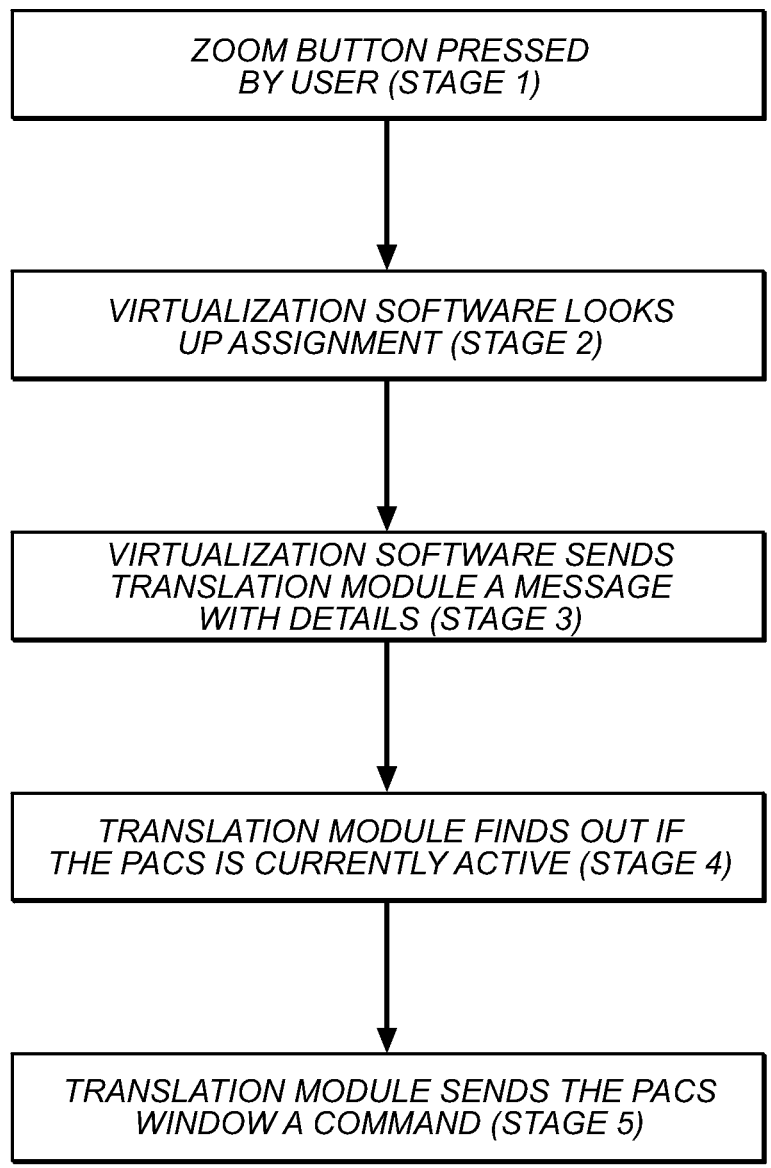
FIGS. 6A-6C show flowcharts of non-limiting exemplary methods for the system of FIG. 2 according to at least some embodiments of the present invention.
Figure 6B:
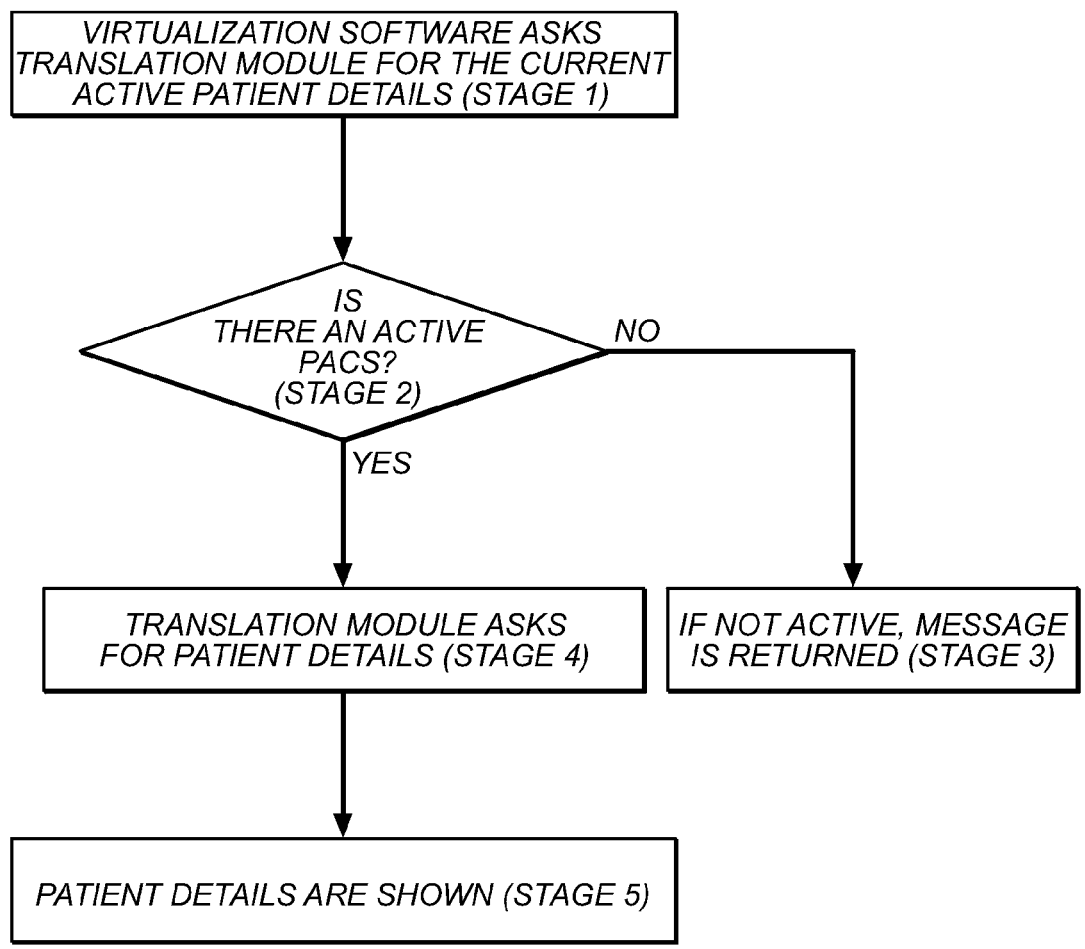
Figure 6C:
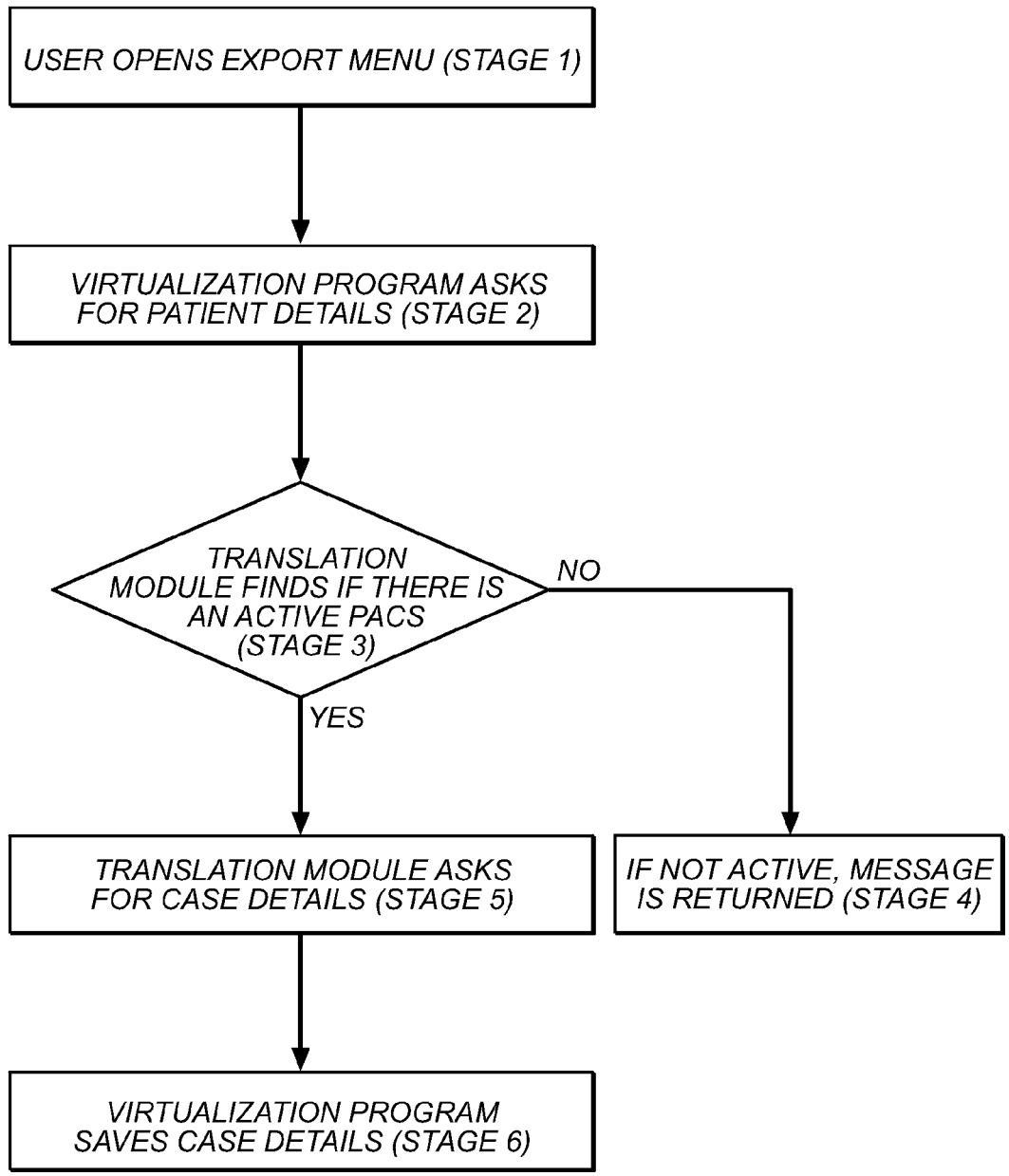

FIGS. 6A-6C show flowcharts of non-limiting exemplary methods for the system of FIG. 2 according to at least some embodiments of the present invention. Optionally, the method may be operative with other systems and also optionally the system of FIG. 2 may be operative with other methods.

Turning now to FIG. 6A, in Stage 1, an interaction element of type button, assigned to "Zoom", is pressed by the user. In Stage 2, the virtualization program on the tablet or other touch screen input device looks up the assignment of the zoom button in the assignment table and discovers the unique ID of the command in the PACS or other interaction software (for this example, the software will be assumed to be PACS for the sake of discussion only and without any intention of being limiting). In Stage 3, the virtualization program sends the translation module a message with the following details: Type of command (button for PACS); Unique ID of command.

In Stage 4, the translation module finds out if the PACS is currently active. If multiple PACS windows are open, it will take the active one.

In Stage 5, the translation module sends the PACS window a command with the unique ID understood by the PACS so that the zoom function occurs.

Turning now to FIG. 6B, in Stage 1, and optionally periodically, the virtualization program asks the translation module for the current active patient details. Such a query may optionally arise from a user command or request, for example. In Stage 2, the translation module finds out if the PACS is currently active. If multiple PACS windows are open, it will take the active one. In Stage 3, if no PACS is active, the translation module sends the virtualization program the answer that no patient is loaded.

In Stage 4, if PACS is active, translation module operates PACS interface and asks for the patient details. These are returned instantly, and are sent through the translation module as an answer to the virtualization program. In Stage 5, the virtualization program shows the patient's details, for example on the screen of the tablet, if available. This is illustrated in the screenshot of FIG. 11.

Turning now to FIG. 6C, in Stage 1, the user opens "export" menu on the virtualization program and asks to save the active patient case as in the description above with reference to FIG. 2B. In Stage 2, the virtualization program sends the translation module a request for the active patient details. In Stage 3, the translation module finds out if the PACS is currently active. If multiple PACS windows are open, it will take the active one. In Stage 4, if no PACS is active, the translation module sends the tablet/input device the answer that no patient is loaded.

In Stage 5, if PACS is active, translation module operates PACS interface and asks for the case details. These are returned instantly, and are sent through the translation module as an answer to the virtualization program. In Stage 6, the virtualization program adds these details to the list of saved cases.

It should be noted that the above method may optionally be performed with a slightly different configuration than that shown in FIG. 2, in which no local PACS is present on the standalone computer, but rather only a thin client is available, for example, a web browser, or other zero footprint software. In this case, all of the actions performed by "PACS" are performed on the remote computer, such as the remote server, which then communicates with the translation module, which may also optionally be on the remote server.

Additionally or alternatively, for such a thin client, while images are optionally and preferably displayed on the standalone computer display, the tablet or other touch screen input device may otherwise optionally handle all of the user interactions, including with regard to any menus or "popup" GUI gadgets.

Figure 7:
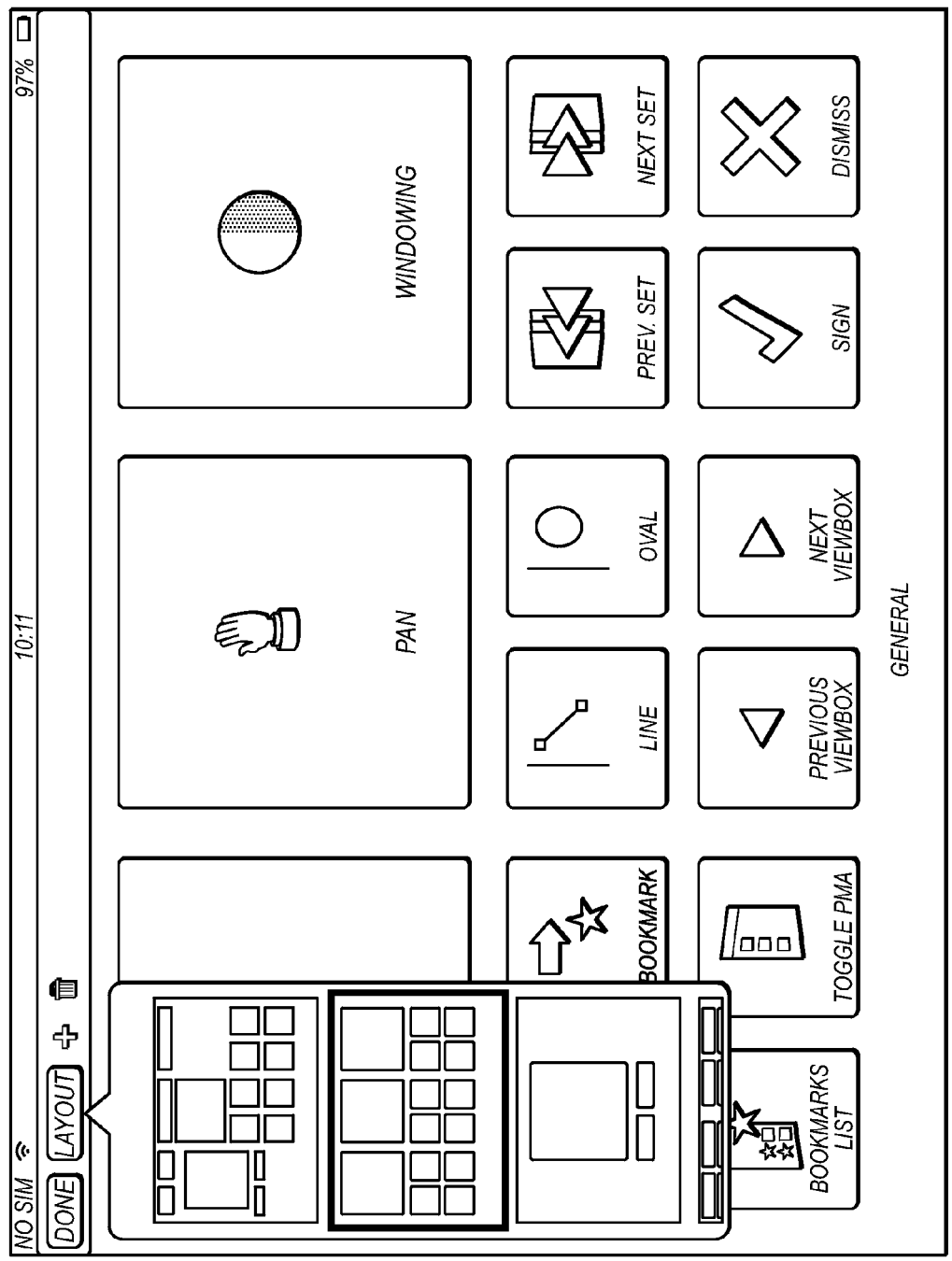
FIG. 7 shows a screenshot of "editing" mode, in which the user may optionally change one or more aspects of the desktop, such as one or more button assignments.

FIG. 7 shows a screenshot of "editing" mode, in which the user may optionally change one or more aspects of the desktop, such as one or more button assignments or optionally also the general layout and number and type of buttons.

Figure 8:
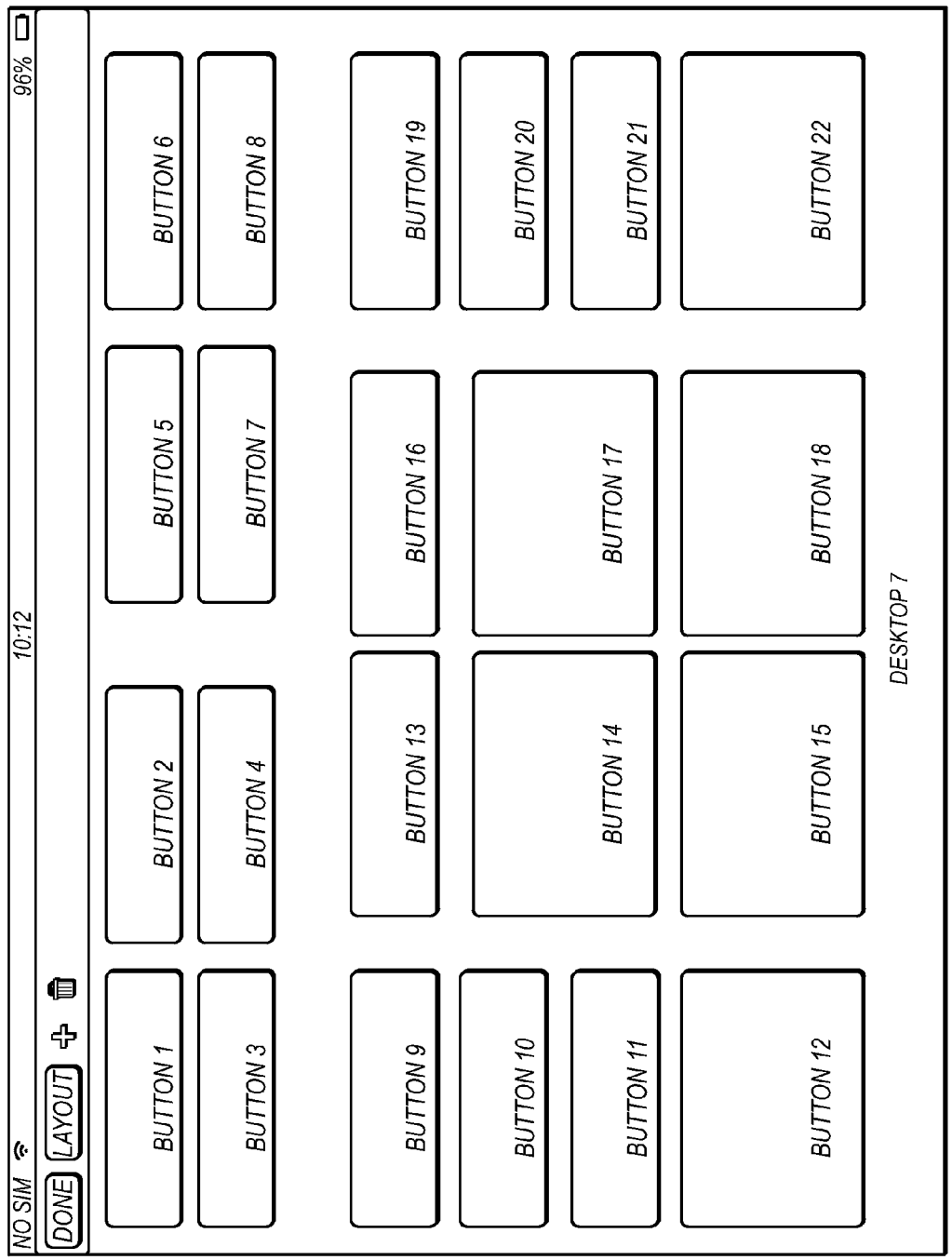
FIG. 8 shows a screenshot of a layout before being populated with interaction elements.

FIG. 8 shows a screenshot of a layout before being populated with interaction elements.

Figure 9A:
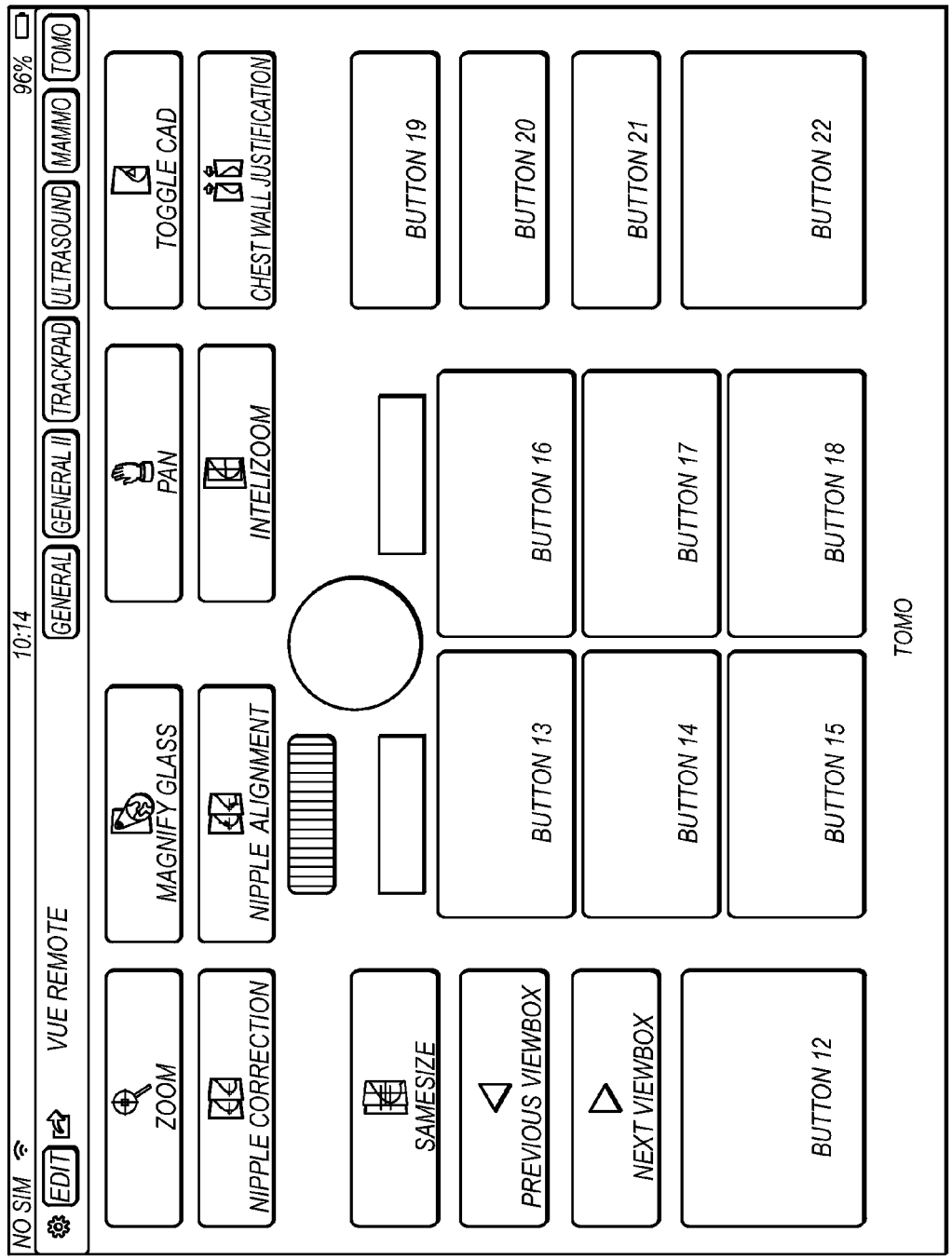
FIGS. 9A-9C show the layout after being populated with at least some interaction elements.
Figure 9B:
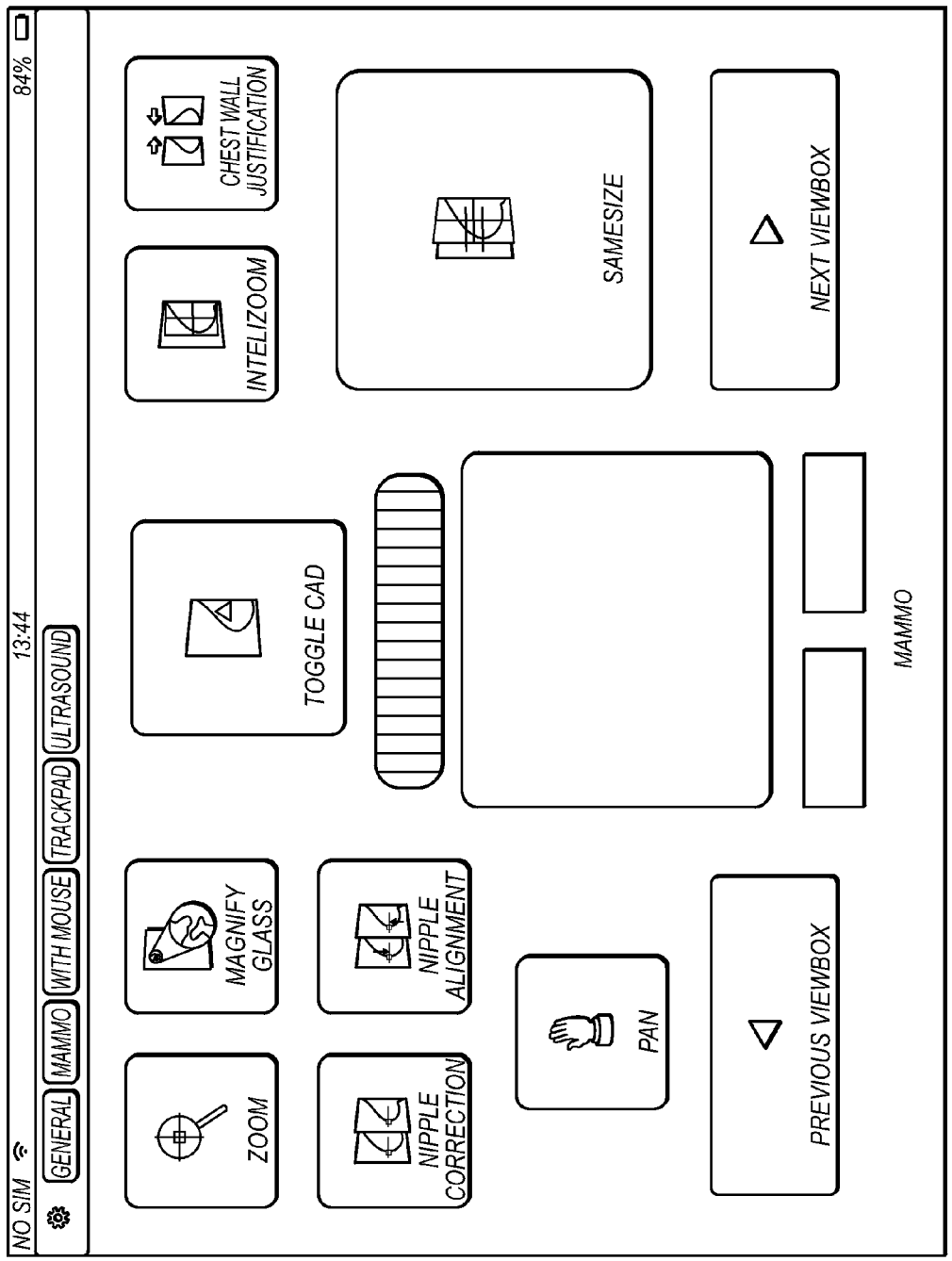
Figure 9C:
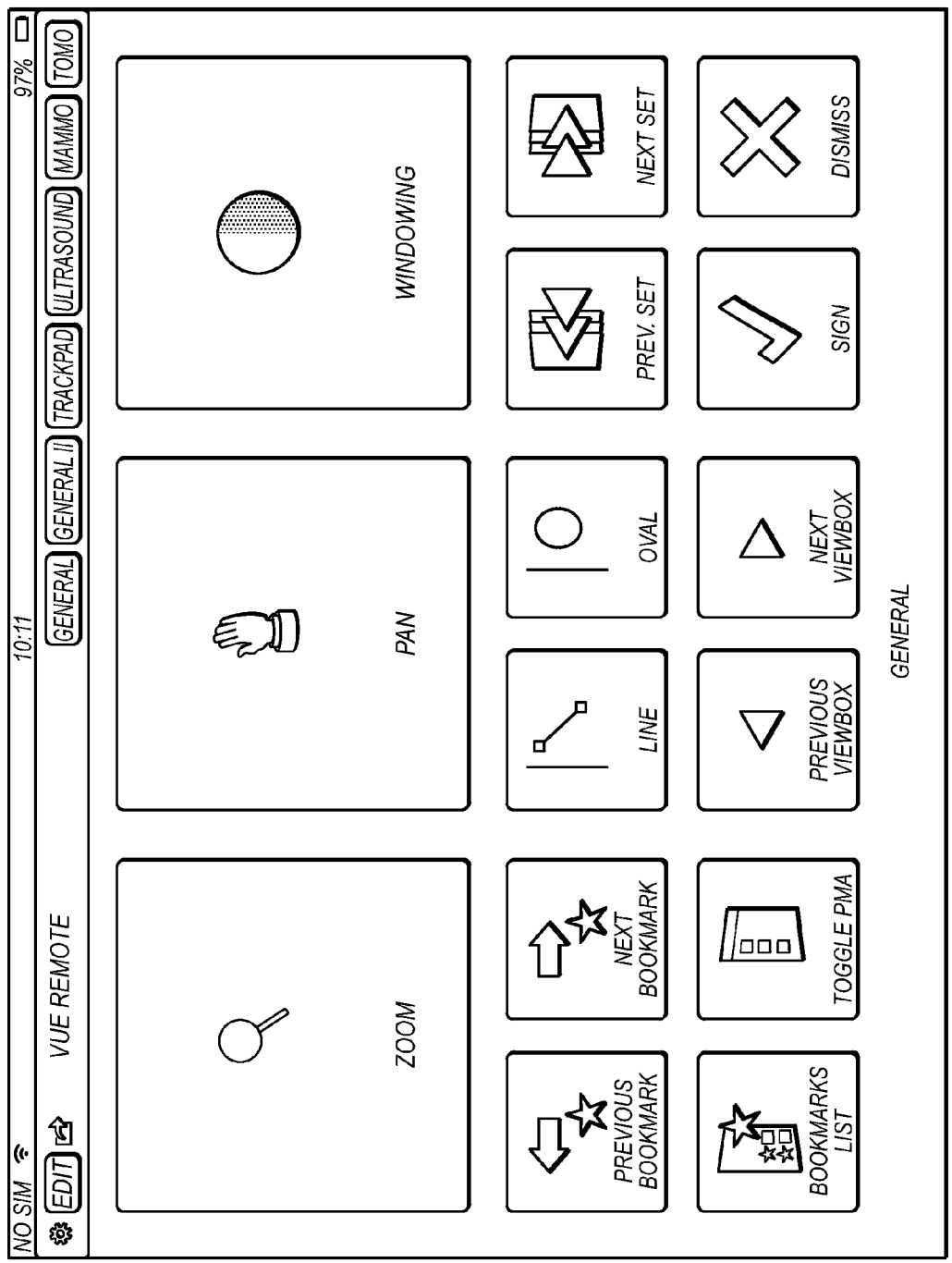

FIGS. 9A-9C show the layout after being populated with at least some interaction elements. FIG. 9A shows the partially populated layout with a trackball; FIG. 9B shows the completely populated layout as a desktop with a trackpad; and FIG. 9C shows the completely populated layout as a desktop with buttons only.

Figure 10:
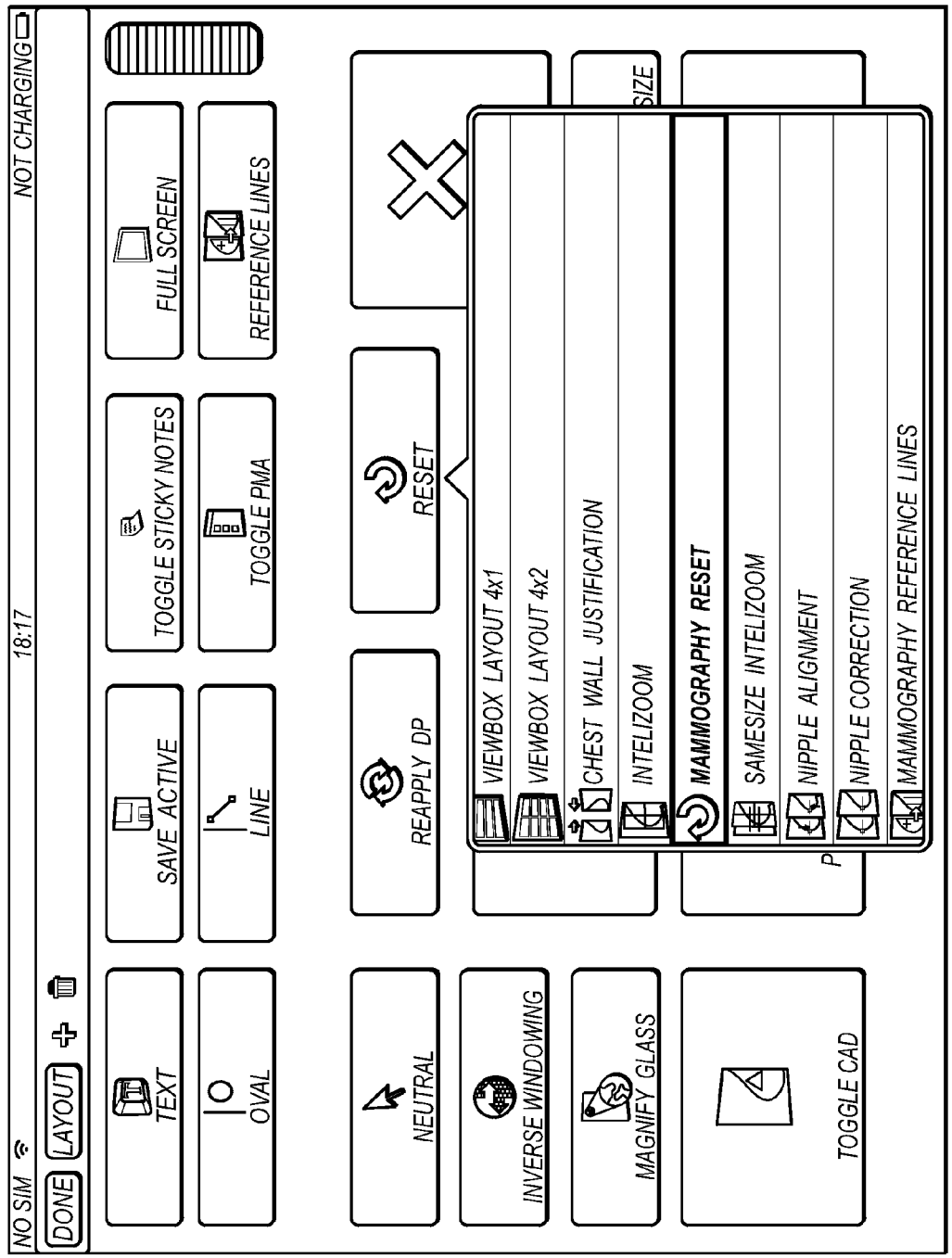
FIG. 10 shows an example of selecting an operation assignment for an interaction element such as a button for example.

FIG. 10 shows an example of selecting an operation assignment for an interaction element such as a button for example.

FIG. 11 shows the ability to obtain further information from the PACS software, in this case a list of active patients.

Figure 12:
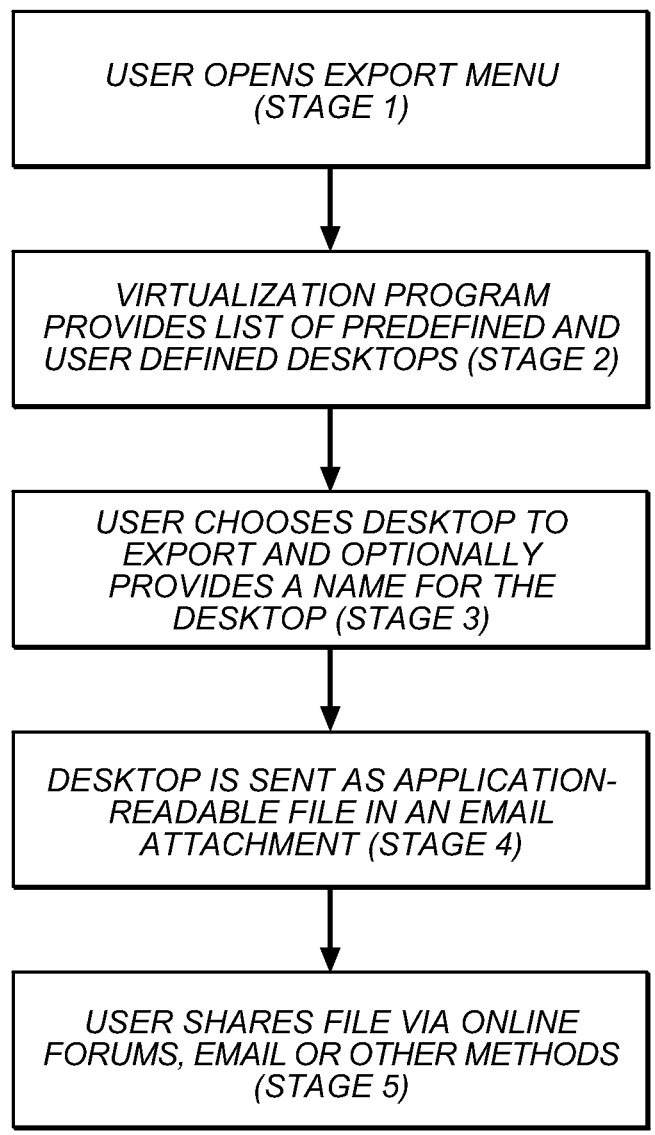
FIG. 12 shows a flowchart of a non-limiting exemplary method for sharing of a particular layout or desktop for a particular type of software or software function with other users according to at least some embodiments of the present invention.

FIG. 12 shows a flowchart of a non-limiting exemplary method for sharing of a particular layout or desktop for a particular type of software or software function with other users according to at least some embodiments of the present invention. In Stage 1 the user opens the "export" menu on the virtualization program in order to choose which desktop to export. In Stage 2 the virtualization program displays a list of predefined and user created desktops that are stored in the layout database 107.

In Stage 3 the user selects the desktop that they wish to export and optionally provides a name for the desktop to be exported. In Stage 4 the application creates a file representing the desktop and attaches this file to an email message which may then be sent using the email client of the tablet. In a non-limiting example, the user may email the desktop file to themselves so that they may further share the file from another computing device (Stage 5). Alternatively, as in Stage 5, the desktop file may be emailed directly and thereby shared with desired recipients.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for controlling a standalone computer operating a medical imaging software program and a standalone computer display, comprising:
   providing a touch screen input device in communication with the standalone computer, the touch screen input device having a display, wherein the touch screen input device and the standalone computer are local;
   providing a desktop, the desktop comprising a configurable layout of a plurality of interaction elements, the plurality of interaction elements controlling functions of the medical imaging software program;
   defining a layout comprising the plurality of interaction elements according to at least one selection by a user, the layout defining a location and type of interaction elements in the desktop;
   defining operation assignments between the interaction elements and functions of the medical imaging software program according to an operation assignment table, wherein the operation assignment table comprises a plurality of operation assignments for invoking a plurality of logical operations relevant to the medical imaging software program, the plurality of logical operations including operations for manipulating medical images;
   displaying the desktop to the user on the display of the touch screen input device; and
   controlling the medical imaging software program by the user through manipulation of one or more of the plurality of interaction elements on the desktop by:
      manipulating at least one interaction element on the desktop by the user,
      transmitting a command from the touch screen input device to the standalone computer according to the manipulated interaction element and according to the operation assignment,
      invoking a function at the medical imaging software program according to the transmitted command, wherein the function is one of the plurality of logical operations defined according to the operation assignment,
      causing the display of the standalone computer to display information to the user according to the invoking the function; and
   operating the interactive software program sequentially on a plurality of standalone computers, such that upon stopping sending commands to a first of the plurality of standalone computers, and starting to send commands to a second of the plurality of standalone computers, the touch screen input device invokes an operation of the interactive software program on the second of the plurality of standalone computers according to a last state of operation on the first of the plurality of standalone computers.

2. The method of claim 1, wherein the layout comprises a specified layout, and the method further comprises specifying the specified layout according to one or more requests of the user.

3. The method of claim 1, wherein the layout comprises a configurable layout, and the method further comprises configuring the configurable layout according to one or more requests of the user.

4. The method of claim 3, further comprising substituting a different layout for a current layout according to a request by the user.

5. The method of claim 1, wherein the layout is determined according to a layout database.

6. The method of claim 5, wherein any changes to the layout are stored in the layout database.

7. The method of claim 1, wherein the interaction element comprises a button, trackball, track pad, mouse, other pointing device or a gestured command on a touch screen.

8. The method of claim 1, further comprising receiving information from the interactive software program by the touch screen input device.

9. The method of claim 1, wherein the touch screen input device comprises a microphone, the method further comprising: receiving verbal dictation from the user; and converting the verbal dictation to text.

10. The method of claim 1, wherein the layout comprises a specified layout, and the method further comprises specifying the specified layout according to one or more requests of the user.

11. The method of claim 1, wherein the layout comprises a configurable layout, and the method further comprises configuring the configurable layout according to one or more requests of the user.

12. The method of claim 1, further comprising receiving information from the medical imaging software program by the touch screen input device.

13. The method of claim 1, wherein the touch screen input device comprises a microphone, further comprising: receiving verbal dictation from the user; and converting the verbal dictation to text.

14. The method of claim 1, wherein the invoking the function at the medical imaging software program further comprises:
   receiving the command by a translation module operated by the standalone computer; and
   translating the command for the medical imaging software program by the translation module.

15. The method of claim 1, further comprising:
   providing a plurality of user-selectable desktops, each of the plurality of user-selectable desktops comprising a predetermined layout of the plurality of interaction elements; and
   allowing a user to select one of the provided plurality of user-selectable desktops.

16. The method of claim 1, wherein the the plurality of logical operations is specific to functions of the medical image processing software.

17. The method of claim 16, further comprising:
   providing a plurality of user-selectable desktops, each of the plurality of user-selectable desktops comprising a predetermined layout of the plurality of interaction elements and operation assignments, wherein each desktop is specific to logical operations for medical image processing software; and
   allowing a user to select one of the provided plurality of user-selectable desktops to form a specific user-selectable desktop.

18. The method of claim 17, further comprising:
   constructing a plurality of user-selectable desktops by a user, each of the plurality of user-selectable desktops comprising a predetermined layout of the plurality of interaction elements and operation assignments, wherein each desktop is specific to logical operations for a particular type of medical image or medical imaging procedure;
   selecting one of the plurality of user-selectable desktops; and
   allowing a user to select one of the provided plurality of user-selectable desktops.

19. The method of claim 1, wherein the touch screen device comprises dynamic physical buttons to create a sensation of a key press.

20. The method of claim 17, further comprising:
   saving a state of the specific user-selectable desktop and of an image being served by a PACS (picture archiving and communication system) module by the user; and
   displaying the specific user-selectable desktop on the touch screen device but the image on a different standalone computer upon receipt of a command from the user.

21. The method of claim 18, further comprising:
   displaying the selection of the specific user-selectable desktop on a tablet computer, wherein user commands are entered through the specific user-selectable desktop on the tablet computer.

22. The method of claim 20, further comprising translating commands between the PACS module and the desktop by a translation module, by mapping the operation assignments to functions of the PACS module by the translation module.

23. The method of claim 22, wherein the translating the commands further comprises analyzing a command from the desktop; if the command relates to a keyboard shortcut, translating the command and sending to the PACS module; and if the command relates to a pointing device command, translating the command and sending the command to an operating system of the standalone computer.

24. The method of claim 1, wherein the touch screen device comprises dynamic physical buttons to create a sensation of a key press.

25. The method of claim 1, further comprising replacing input from the user through an input device to the standalone computer by input through the touch screen input device.

26. The method of claim 1, further comprising receiving input voice data from the touch screen input device, wherein the touch screen input device does not analyze the voice data.

27. The method of claim 1, wherein the standalone computer and the touch screen input device are local to each other and to the user, such that the user is able to view the display of the standalone computer while simultaneously viewing the display of the touch screen input device.

28. The method of claim 1, wherein the standalone computer further comprises a separate keyboard or pointing device, or both, wherein the touch screen input device does not include a separate keyboard or pointing device.

* * * * *